United States Patent [19]

Rifkin

[11] 4,311,562
[45] Jan. 19, 1982

[54] METHOD FOR INHIBITING DEPOSIT FORMATION IN PROCESS EQUIPMENT ASSOCIATED WITH SEPARATION AND PURIFICATION OF ALKYL PHOSPHOROCHLORIDOTHIOATES

[75] Inventor: Ellis B. Rifkin, Southfield, Mich.

[73] Assignee: Ethyl Corporation, Richmond, Va.

[21] Appl. No.: 207,770

[22] Filed: Nov. 17, 1980

[51] Int. Cl.³ .................... B01D 3/34; C23F 11/00; C23F 14/00
[52] U.S. Cl. ................................. 203/7; 260/989; 260/990
[58] Field of Search ............... 252/51.5 R; 260/981, 260/980, 960, 986, 989, 990; 159/DIG. 13; 202/DIG. 1; 203/6, 7

[56] References Cited

U.S. PATENT DOCUMENTS 3,794,703  2/1974  Beck et al. .................... 260/990

Primary Examiner—Frank Sever
Attorney, Agent, or Firm—Donald L. Johnson; Joseph D. Odenweller; John F. Hunt

[57] ABSTRACT

Deposit formation in distillation units, particularly column reboiler units, associated with the separation and purification of dialkyl phosphorochloridothioates from a crude material containing oxygenated compound impurities, is inhibited by incorporating in the feed stock a minor proportion (generally about 0.05 to about 15.0 weight percent) of the condensation product of phenol, and preferably a high molecular weight alkylphenol, an aldehyde and an amine having a H—N< group.

21 Claims, No Drawings

METHOD FOR INHIBITING DEPOSIT FORMATION IN PROCESS EQUIPMENT ASSOCIATED WITH SEPARATION AND PURIFICATION OF ALKYL PHOSPHOROCHLORIDOTHIOATES

BACKGROUND OF THE INVENTION

The present invention relates to a method for reducing and/or preventing the fouling of process equipment in the preparation of O,O-di($C_1$-$C_8$ alkyl) phosphorochloridothioates. It is particularly applicable to process equipment involving the separation and purification of O,O-di($C_1$-$C_8$ alkyl) phosphorochloridothioates from a mixture thereof with certain impurities. Preferably, the improved method comprises adding to the crude dialkyl phosphorochloridothioate the condensation product of a phenol and preferably a high molecular weight alkylphenol, an aldehyde and an amine containing at least one H—N<group. The O,O-dialkyl phosphorochloridothioates are valuable intermediates, for instance, in the preparation of lubricant additives and insecticides. Particularly, O,O-diethyl thiophosphoryl chloride is an intermediate in the synthesis of an insecticide known as parathion, and O,O-dimethyl thiophosphoryl chloride is an intermediate in the synthesis of the insecticide called methyl parathion. Such are also useful in the manufacture of diazinon, chlorpyrifus, fensulfothion and the like.

Several methods have been used for the synthesis of the esters of phosphorochloridothioic acid including one-step and two-step methods. In the one-step process, phosphorus pentasulfide, alcohol and chlorine are reacted to prepare the ester corresponding to the alcohol and then the solvent is removed and the product separated. Typical prior art patents disclosing a one-step process include U.S. Pat. Nos. 3,356,774 and 3,502,750. U.S. Pat. No. 3,356,774 discloses reacting a phosphorus pentasulfide suspension in an inert solvent at a temperature within the range of about 0° C. to about 150° C. with chlorine and an alcohol having 1 to 6 carbon atoms by introducing a stream of chlorine into said suspension and adding dropwise concurrently therewith the alcohol, allowing the chlorinating reaction to proceed to completion, expelling the solvent from the resulting reaction mixture and isolating O,O-dialkylthionophosphoric acid chloride by distillation. U.S. Pat. No. 3,502,750 discloses preparing lower alkyl esters of phosphorochloridothioic acid by reacting chlorine with a lower alkyl ester of dithiophosphoric acid and freeing the product of sulfur monochloride by reaction with hydrogen sulfide, preferably formed during the production of the dithiophosphoric acid ester by reaction of a lower alkanol with phosphorus pentasulfide.

In the two-step process, the first process step reacts phosphorus pentasulfide with an alcohol, such as ethanol, so as to form O,O-diethyl dithiophosphoric acid and hydrogen sulfide, and in a second process step the isolated O,O-diethyl dithiophosphoric acid is chlorinated in an appropriate solvent with chlorine gas, resulting in the formation of O,O-diethyl thiophosphoric acid chloride. Examples of prior art patents disclosing a two-step process include U.S. Pat. Nos. 3,836,610 and 3,856,898. In U.S. Pat. No. 3,836,610, the reaction mixture is chlorinated and then established and maintained at a temperature in the range of 85° C.–110° C. until it is substantially free of sulfur monochloride and the relatively thermal unstable sulfur that forms becomes more thermally stable so that the product dialkyl thiophosphoryl chloride can be readily and safely removed from the mixture thereof with sulfur by distillation. U.S. Pat. No. 3,856,898 discloses a process for treating a mixture comprising O,O-di($C_1$-$C_8$ alkyl) phosphorochloridothioate and amphorous sulfur at a concentration up to about one-third of the weight of the phosphorochloridothioate. In this process, the mixture is established in a first temperature range in which substantially all of the sulfur can go into solution without substantial decomposition of the phosphorochloridothioate, and maintained in that range until substantially all of the sulfur does go into solution. The resulting solution is established in a temperature range in which dissolved sulfur crystallizes, and is maintained in that range until sulfur crystallization is substantially complete. The crystallized sulfur then is separated by settlement (filtration, decantation, centrifugation, or the like) from the mother liquor. In one embodiment, the mother liquor, composed of the phosphorochloridothioate dissolved in a solvent, is treated by a procedure which includes distillation to obtain O,O-di($C_1$-$C_8$ alkyl) phosphorochloridothioate. Other prior art patents which disclose processes for preparing O,O-dialkyl phosphorochloridothioates include U.S. Pat. No. 3,897,523 which teaches a purification process in which the crude dialkyl phosphorochloridothioate is vaporized in a film evaporator, the vapor is condensed, washed with water at 10° C. to 60° C., the organic and aqueous phases separated and the organic phase vacuum dried; and U.S. Pat. No. 4,025,586, which discloses distilling the product dialkyl phosphorochloridothioate and water washing the distillation residue to hydrolyze impurities. The washed residue is then dried and recycled to the chlorination step. U.S. Pat. No. 3,089,890, teaches treating a distilled crude phosphorochloridothioate with water, separating the organic phase and drying to upgrade the crude and recover substantially contaminant-free phosphorochloridothioate. Most recently, U.S. Pat. No. 4,159,289 teaches a process for removal of sulfur impurities from phosphorochloridothioates by distillation in the presence of a naphthalenic liquid hydrocarbon sulfur solubilizing or suspending agent.

Conventionally, the alkyl groups in the dialkyl phosphorchloridothioates have from 1 to 8 carbon atoms and are generally selected from methyl, ethyl, isopropyl, butyl, sec.butyl, t-butyl, and the like, up through n-octyl and isomers thereof. In each of these conventional one-step and two-step processes, however, impurities, such as phosphates are produced which causes severe fouling of the process equipment during separation and purification of product dialkyl phosphorochloridothioates. Although these various processes differ somewhat as to the precise manner in which product dialkyl phosphororochloridothioates are produced, those processes which involve the heating of a crude feed stock to a high temperature and the passage of such heated stock through a distillation column to separate and recover product dialkyl phosphorochloridothioate from the crude feed stock almost always result in the formation of some undesirable materials, believed principally to comprise oxygenated phosphorous compound impurities produced during production of the phosphorochloridothioates as by-products or from the thermal degradation of the desired dialkyl phosphorochloridothioates during purification, along with impurities other than the aforementioned oxygenated phosphorus type impurities such as iron and/or sulfur or iron and sulfur containing compounds. These impurities solidify in and plug the distillation columns, and adhere to the walls of the tubes in the column reboiler sections of the columns as the impurities containing crude feed stock passes through or around the tubes. This lowers the efficiency, principally by impeding the flow of the feed stock therethrough, and the transfer of heat to or from such stock. After enough material has accumulated on the various parts on the reboiler units, usually the tube portions thereof, to lower efficiency substantially, the unit must be dismantled, cleaned and reassembled. Of course, such cleaning operations are not only tedious and costly, but result in a large proportion of "down-time" during which the unit is not functioning. Distillation alone cannot adequately remove these impurities.

The deposit formations resulting from the fouling phenomenon consist of a tacky, water soluble tar material believed to be composed principally of polyphosphates produced during the production of the phosphorochloridothioates as by-products aforediscussed and/or from the desired product dialkyl phosphorochloridothioates which may be thermally degraded over time in the purification equipment to produce additional by-products of the same sort. Specific impurities which are formed include diethylchlorophosphate, triethylthiophosphate, ethyldichlorophosphate and ethyldichlorothiophosphate. The thermal degradation of diethyl phosphorochloridothioate is illustrative of what may occur during processing operations. A sample of diethyl phosphorochloridothioate was found to contain 88.4 area percent diethyl phosphorochloridothioate and 0.48 area percent diethyl phosphoryl chloride by vapor phase chromatography. The sample was split in two parts and one was purged with air while the other was purged with nitrogen. The samples were heated at 140° C. for 4 hours. Samples taken after one-half hour and 3 hours were analyzed with the results shown below:

| Increase of Oxygenated Phosphorus Impuritites with Time at 140° C. | | | |
|---|---|---|---|
| | Time, hrs. | | |
| | 0 | ½ | 3 |
| Air Purge | | | |
| Diethylphosphorochlorido-thioate (Area %) | 88.4 | 87.3 | 78.9 |
| Diethylphosphoryl chloride (Area %) | 0.48 | 0.59 | 2.4 |
| N₂ Purge | | | |
| Diethylphoschlorochlorido-thioate (Area %) | 88.4 | 87.1 | 71.4 |
| Diethylphosphoryl chloride (Area %) | 0.48 | 0.68 | 2.3 |

From the above data, it is clear that the impurity has increased fivefold while where was a 9-20% decrease in desired product. Such high impurity levels are not only undesirable for the aforediscussed fouling problems which they create in the distillation equipment, but are also undesirable because the end-product insecticides have been registered with governmental agencies as having been tested and found safe and effective with certain impurities at not greater than certain concentrations. Therefore, it is critical not only to prevent the fouling of process equipment by the impurities but also to maintain impurity identities and levels at or below those allowed in governmental registrations and as stated on label certifications for the end product.

Without limiting the invention in any manner and without advocating any particular mechanism or theory of action, it is believed that degradation of dialkyl phosphorochloridothioates could possibly take place according to the following chemical reaction scheme:

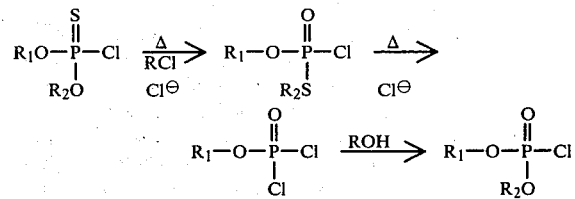

where $R_1$ and $R_2$ can be the same or different $C_{1-8}$ alkyl groups, the temperature ranges from 100°–150° C., and the necessary contact with ionic species is provided for a time sufficient to facilitate the degradation reaction. Further, it is believed that the presence of other impurities, such as sulfur, for example, in the form either of free sulfur or in some other form such as sulfur monochloride, formed as a by-product during the reaction; and/or iron which may be present in the crude feedstock or originate from deterioration of the metal in the process equipment may also either constitute a portion of the fouling deposits or alternatively exert a catalytic effect on and promote or increase the rate of phosphorus impurities formation. While fouling sometimes may be controlled by careful processing to obtain high purity crude feedstock by excluding impurities from the crude feed prior to separation and purification of product dialkyl phosphorochloridothioate therefrom, this is not altogether possible nor economically feasible in plant scale operation on a regular continuing basis. One method for removing dialkyl phosphorochloridothioates impurities from a crude feed stock containing same is disclosed in U.S. Appl. Ser. No. 073,684, filed Sept. 10, 1979 which teaches treating the crude feed stock with an alcohol having from 2 to 30 carbon atoms so that the impurities and the alcohol from a reaction product having sufficiently different physical properties to promote the separation of product dialkyl phosphorochloridothioates from the resulting mixture.

Invention

It has now been found that deposit formation in the distillation units, particularly column reboiler units, used in the separation and purification of dialkyl phosphorochloridothioates from a crude mixture thereof containing certain oxygenated phosphorous compound impurities, can be prevented and/or inhibited simply, without additional capital cost and with very small operational cost, by the addition to the crude dialkyl phosphorochloridothioate of a suitable treating agent.

Accordingly, it is an object of the present invention to inhibit and/or prevent the deposition and accumulation of harmful oxygenated phosphorus compound impurities in the distillation equipment, particularly the column reboiler units associated with the separation and purification of dialkyl phosphorochloridothioates formed during the separation and purification of product dialkyl phosphorochloridothioate from a crude feed stock thereof containing said oxygenated phosphorus compound impurities.

It is another object of the present invention to suspend or dissolve said oxygenated phosphorus compound impurities formed during the preparation and purification of product dialkyl phosphorochloridothioates in said feed stock thereby inhibiting their deposition and accumulation on various parts of the distillation equipment associated with the separation and purification of product dialkyl phosphorochloridothioates from a crude mixture thereof containing said oxygenated phosphorus compound impurities and allowing their removal from the column bottoms with the waste stream thereby leaving the column and column reboiler clean.

Yet another object of the present invention is to reduce the amount of "down-time" in the operation of the distillation equipment associated with the separation and purification of product dialkyl phosphorochloridothioates from a crude mixture thereof containing oxygenated phosphorus compound impurities thereby permitting the continuous distillation of said product dialkyl phosphorochloridothioates and thus avoiding batch distillation.

These and other objects of the invention are realized by the provision of a method for inhibiting or preventing the deposition and/or accumulation of oxygenated phosphorus compound impurities in the distillation column and column reboiler unit during the passage therethrough of a crude feed stock containing product dialkyl phosphorochloridothioates admixed with deposit-forming and fouling-causing oxygenated phosphorus compound impurities by dissolving in said feed stock a minor proportion, generally at least about 0.05 weight percent to about 15.0 weight percent and preferably about 0.1 weight percent to about 10.0 weight percent of the reaction products of a phenol and preferably a high molecular weight alkylphenol, an aldehyde and an amine containing at least one H—N group.

Accordingly, a preferred embodiment of the present invention is a method for inhibiting or preventing the accumulation of oxygenated phosphorus compound impurities in the distillation columns and column reboiler units associated with the separation and purification of O,O-dialkyl phosphorochloridothioates from a crude feed stock containing said O,O-dialkyl phosphorochloridothioates admixed with deposit-forming and fouling-causing oxygenated phosphorus compound impurities which comprises distilling said O,O-dialkyl phosphorochloridothioate containing feed stock in the presence of a minor proportion of the reaction product of:

A. one mole part of an alkylphenol having the formula:

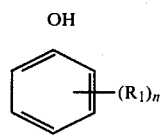

wherein n is an integer from 1 to 2, and $R_1$ is an aliphatic hydrocarbon radical having a molecular weight of from about 400 to 1500;

B. from 1-5 mole parts of an aldehyde having the formula:

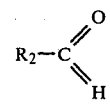

wherein $R_2$ is selected from hydrogen and alkyl radicals containing 1-6 carbon atoms; and C. from 0.5-5 mole parts of an amine having at least one H—N group.

In general, the process of the present invention proceeds initially as in any of the inherent above prior art patents until the step of separation of the product dialkyl phosphorochloridothioates from the reaction mixture. Accordingly, each of the above-mentioned patents contains valuable process information regarding the production of crude dialkyl phosphorochloridothioate useful in the practice of the present invention and the teachings of those references are hereby incorporated by reference as if fully set forth. The advantage obtained in the improved process of this invention is that the addition to the dialkyl phosphorochloridothioate containing crude of the aforementioned condensation products prevents or inhibits the accumulation of deposits in the continuous distillation column and column reboiler units formed primarily from oxygenated phosphorus compound impurities present in the crude feed stock during the separation and purification of product of dialkyl phosphorochloridothioate. The addition of the treating agent to the feed stock allows the use of a continuous column distillation system, reduces the amount of "down-time" in the operation of the continuous distillation train, and provides a bottoms stream which contains the waste materials in a fluid or suspended state thereby allowing the product to be recovered from the overhead system and the waste stream to be easily removed for treatment or recycle. Typically, the crude dialkyl phosphorochloridothioates can have up to about 3% by weight of oxygenated phosphorus compounds, for example, diethyl chlorophosphate. Additionally, after formation, exposure of the product dialkyl phosphorochloridothioate to heat causes degradation and increases impurities such as dialkyl chlorophosphates. For example, distillation of diethyl chlorophosphate can increase the amount of diethyl phosphoryl chloride (i.e., diethyl chlorophosphate). Further, as aforementioned it is believed that the presence of other impurities, such as sulfur, for example, either in the form of free sulfur or in some other form, such as sulfur monochloride, formed as a by-product during the reaction; and/or iron, which may be present either in the crude feedstock or originate from deterioration of the metal in the process equipment may also contribute to the fouling deposits or, alternatively, exert a catalytic effect on and promote or increase the rate of phosphorus impurities formation. However, when separation or purification takes place in the presence of the aforedescribed condensation products as disclosed in the present process, there is a marked decrease in the amount of oxygenated phosphorus compound impurities which accumulate in, and eventually plug, the distillation equipment, i.e. the distillation column and column reboiler. Without being limited by any form or mode of action or theoretical mechanism of the invention, it is believed that the condensation products of the present invention react with the oxygenated phosphorus impurities selectively, altering their physical and/or chemical properties and allows the impurities to remain suspended or dissolved in the crude feed stock during separation and purification of the product dialkyl phosphorochloridothioates by means of conventional techniques. Any treating agent remaining after separation and purification of product diakyl phosphorochloridothioates, remains suspended or dissolved in the bottoms stream which contains all of the waste materials in a fluid or suspended state and is eventually removed from the column bottoms where it is treated for waste disposal and/or recycle. Under these conditions, the impurities can be readily removed from the column bottoms with the waste stream, leaving the distillation column and column reboiler clean and the waste stream in an easily handled, pumpable form.

Thus, the condensation product additive useful in this invention is one which when reacted with oxygenated phosphorus compound impurities produced in a process for preparing dialkyl phosphorochloridothioates will so alter the physical and chemical properties of the impurities by producing a reaction product that conventional techniques can be used to separate the reaction product from the dialkyl phosphorochloridothioate and that said impurities will not deposit in and foul the distillation equipment associated with the separation and purification of the desired dialkyl phosphorochloridothioate product.

The condensation products required for the purpose of this invention are described in detail in U.S. Pat. No. 3,948,619. In the interest of not unduly lengthening the present specification it is intended that the disclosure of the said U.S. Pat. No. 3,948,619 be considered as forming a part of the present specification.

The anti-fouling additives of the present invention are made by condensing a phenol and preferably a high molecular weight alkylphenol, an aldehyde and ammonia or preferably an aliphatic amine having at least one reactive hydrogen atom bonded to nitrogen. In other words, an amine having at least one H—N< group. This reaction is the well-known "Mannich reaction" (see "Organic Reactions," Volume 1). The conditions for carrying out such a condensation are well known.

The preferred alkylphenol reactant is an alkylphenol wherein the alkyl radical has an average molecular weight of from about 400 to 1500. In a more preferred alkylphenol reactant the alkyl radical has an average molecular weight of from about 800 to 1300, and in the most preferred alkylphenols the alkyl radical has an average molecular weight of from about 900 to 1100.

Alkylphenols suitable for use in the preparation of the present treating agents are readily prepared by adaptation of methods well known in the art. For example, they may be prepared by the acid catalyzed alkylation of phenol with an olefin. In this method, a small amount of an acid catalyst such as sulfuric or phosphoric acid, or preferably a Lewis acid such as $BF_3$-etherate, $BF_3$-phenate complex or $AlCl_2$-$HSO_4$, is added to the phenol and the olefin then added to the phenol at temperatures ranging from about 0° up to 200° C. A preferred temperature range for this alkylation is from about 25° C. to 150° C., and the most preferred range is from about 50° to 100° C. The alkylation is readily carried out at atmospheric pressures, but if higher temperatures are employed the alkylation may be carried out at super atmospheric pressures up to about 1000 psig.

The alkylation of phenols produces a mixture of mono-, di- and tri-alkylated phenols. Although the preferred reactants are the mono-alkylated phenols, the alkylation mixture can be used without removing the higher alkylation products. The alkylation mixture formed by alkylating phenol with an olefin using an acid catalyst can be merely water washed to remove the unalkylated phenol and the acid catalyst and then used in the condensation reaction without removing the di- and tri-alkylated phenol products. The di-alkylated phenol enters into the condensation reaction and yields useful treating agents. Another method of removing the unreacted phenol is to distill it out, preferably using steam distillation or under vacuum, after washing out the alkylation catalyst. The amount of di- and tri-alkylated phenols can be kept at a minimum by restricting the amount of olefin reactant added to the phenol. Good results are obtained when the mole ratio of olefin to phenol is about 0.25 moles of olefin per mole of phenol to 1.0 mole of olefin per mole of phenol. A more preferred ratio is from about 0.33 to 0.9, and a most preferred ratio is from about 0.5 to 0.67 moles of olefin per mole of phenol.

The olefin reactant used to alkylate the phenol is preferably a monoolefin with an average molecular weight of from about 400 to 1500. The more preferred olefins are those formed from the polymerization of low molecular weight olefins containing from about 2 to 10 carbon atoms, such as ethylene, propylene, butylene, pentene and decene. These result in polyalkene substituted phenols. A most preferred olefin is that made by the polymerization of propylene or butene to produce a polypropylene or polybutene mixture with an average molecular weight of from about 900-1100. This gives the highly preferred polypropylene and polybutene substituted phenols.

The aldehyde reactant preferably contains from 1 to 7 carbon atoms. Examples are formaldehyde, acetaldehyde, propionaldehyde, butyradlehyde, valeraldehyde, hexaldehyde and heptaldehyde. The more preferred aldehyde reactants are the low molecular weight aliphatic aldehydes containing from 1 to about 4 carbon atoms such as formaldehyde, acetaldehyde, butyraldehyde and isobutyraldehyde. The most preferred aldehyde reactant is formaldehyde, which may be used in its monomeric or its polymeric form such as paraformaldehyde.

The amine reactants include those that contain at least one active hydrogen atom bonded to an amino nitrogen atom, such that they can partake in a Mannich condensation. They may be primary amines, secondary amines or may contain both primary and secondary amino groups. Examples include the primary alkyl amines such as methyl amine, ethyl amine, n-propyl amine, isopropyl amine, n-butyl amine, isobutyl amine, 2-ethylhexyl amine, dodecyl amine, stearyl amine, eicosyl amine, triacontyl amine, pentacontyl amine, and the like, including those in which the alkyl group contains from 1 to about 50 carbon atoms. Also, dialkyl amines may be used such as dimethyl amine, diethyl amine, methylethyl amine, methylbutyl amine, di-n-hexyl amine, methyl dodecyl amine, dieicosyl amine, methyl triacontyl amine, dipentacontyl amine, and the like, including mixtures thereof.

Another useful class is the N-substituted compounds such as the N-alkyl imidazolidines and pyrimidines. Also, aromatic amines having a reactive hydrogen atom attached to nitrogen can be used. These include aniline, N-methyl aniline, ortho, meta, and para phenylene diamines, α-naphthyl amine, N-isopropyl phenylene diamine, and the like. Secondary heterocyclic amines are likewise useful including morpholine, thiomorpholine, pyrrole, pyrroline, pyrrolidine, indole, pyrazole, pyrazoline, pyrazolidine, imidazole, imidazoline, imidazolidine, piperidine, phenoxazine, phenathiazine, and mixtures thereof, including their substituted homologs in which the substituent groups include alkyl, aryl, alkaryl, aralkyl, cycloalkyl, and the like.

A preferred class of amine reactants is the diamines represented by the formula:

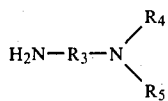

wherein $R_3$ is a divalent alkylene radical containing 1–6 carbon atoms, and $R_4$ and $R_5$ are selected from the group consisting of alkyl radicals containing from 1–6 carbon atoms and radicals having the formula:

$$-R_6-X$$

wherein $R_6$ is a divalent alkylene radical containing from 1–6 carbon atoms, and X is selected from the group consisting of the hydroxyl radical and the amine radical.

The term "divalent alkylene radical" as used herein means a divalent saturated aliphatic hydrocarbon radical having the empirical formula:

$$-C_nH_{2n}-$$

wherein n is an integer from 1 to about 6. Preferably, $R_3$ is a lower alkylene radical such as the $-C_2H_4-$, $-C_3H_6-$, or $-C_4H_8-$ groups. The two amine groups may be bonded to the same or different carbon atoms. Some examples of diamine reactants where the amine groups are attached to the same carbon atoms of the alkylene radical $R_3$ are N,N-dialkyl-methylenediamine, N,N-dialkanol-1,3-ethanediamine, and N,N-di(aminoalkyl)-2,2-propanediamine.

Some examples of diamine reactants in which the amine groups are bonded to adjacent carbon atoms of the $R_3$ alkylene radical are N,N-dialkyl-1,2-ethanediamine, N,N-dialkanol-1,2-propanediamine, N,N-di(aminoalkyl)-2,3-butanediamine, and N,N-dialkyl-2,3-(4-methylpentane)diamine.

Some examples of diamine reactants in which the amine groups are bonded to carbon atoms on the alkylene radical represented by $R_3$ which are removed from each other by one or more intervening carbon atoms are N,N-dialkyl-1,3-propanediamine, N,N-dialkanol-1,3-butanediamine, N,N-dilaminoalkyl)-1,4-butanediamine, and N,N-dialkyl-1,3-hexanediamine.

As previously stated, $R_4$ and $R_5$ are alkyl radicals containing 1 to 6 carbon atoms or alkyl radicals containing 1 to 6 carbon atoms or alkyl radicals containing 1 to 6 carbon atoms which are substituted with the hydroxyl or amine radical. Some examples of hydroxyl substituted radicals are 2-hydroxy-n-propyl, 2-hydroxyethyl, 2-hydroxy-n-hexyl, 3-hydroxy-n-propyl, 4-hydroxy-3-ethyl-n-butyl, and the like. Some examples of amine substituted $R_4$ and $R_5$ radicals are 2-aminoethyl, 2-amino-n-propyl, 4-amino-n-butyl, 4-amino-3,3-dimethyl-n-butyl, 6-amino-n-hexyl, and the like. Preferred $R_4$ and $R_5$ radicals are unsubstituted alkyl radicals such as methyl, ethyl, n-propyl, isopropyl, sec-butyl, n-amyl, n-hexyl, 2-methyl-n-pentyl, and the like. The most preferred $R_4$ and $_{45}$ substituents are methyl radicals.

Some specific examples of diamine reactants are: N,N-dimethyl-1,3-propanediamine; N,N-dibutyl-1,3-propanediamine; N,N-dihexyl-1,3-propanediamine; N,N-dimethyl-1,2-propanediamine; N,N-dimethyl-1,1-propanediamine; N,N-dimethyl-1,3-hexanediamine; N,N-dimethyl-1,3-butanediamine; N,N-di(2-hydroxyethyl)-1,3-propane, diamine; N,N-di(2-hydroxybutyl)-1,3-propanediamine; N,N-di-(6-hydroxyhexyl)-1,1-hexanediamine; N,N-di(2-aminoethyl)-1,3-propanediamine; N,N-di(2-amino-n-hexyl)-1,2-butanediamine; N,N-di(4-amino-3,3-di-methyl-n-butyl)-4-methyl-1,3-pentanediamine; and N-(2-hydroxyethyl)-N-(2-aminoethyl)-1,3-propanediamine.

Another very useful class of amine reactants is the alkylene polyamines which have the formula:

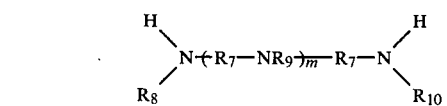

wherein $R_8$, $R_9$ and $R_{10}$ are selected from hydrogen and lower alkyl radicals containing 1–4 carbon atoms, and $R_7$ is a divalent saturated aliphatic hydrocarbon radical containing from 2 to about 4 carbon atoms and m is an integer from 0 to about 4. Examples of these are ethylene diamine, diethylene triamine, propylene diamine, dipropylene triamine, tripropylene tetramine, tetrapropylene pentamine, butylene diamine, dibutylene triamine, diisobutylene triamine, tributylene tetramine, and the like, including the N-$C_{1-4}$ alkyl-substituted homologs.

A most preferred class of amine reactants is the ethylene polyamines. These are described in detail in Kirk-Othmer, "Encyclopedia of Chemical Technology," Vol. 5, pages 898–9, Insterscience Publishers, Inc., New York. These include the series ethylene diamine, diethylene triamine, triethylene tetramine, tetraethylene pentamine, pentaethylene hexamine, and the like. A particularly preferred additive comprises the alkylphenol and aldehyde reactants as described herein in which the amine reactant is a mixture of ethylene polyamines containing a substantial amount of triethylene tetramine and tetraethylene pentamine.

The condensation products are easily prepared by mixing together the alkylphenol, the aldehyde reactant and the amine reactant, and heating them to a temperature sufficient to cause the reaction to occur. The reaction may be carried out without any solvent, but the use of a solvent is usually preferred. Preferred solvents are the water immiscible solvents including water-insoluble alcohols (e.g., amyl alcohol) and hydrocarbons. The more preferred water-immiscible solvents are hydrocarbon solvents boiling from 50° to about 200° C. Highly preferred solvents are the aromatic hydrocarbon solvents such as benzene, toluene, xylene, and the like. Of these, the most preferred solvent is toluene. The amount of solvent employed is not critical. Good results are obtained when from one to about 50 percent of the reaction mass is solvent. A more preferred quantity is from 3 to about 25 percent, and a most preferred quantity of solvent is from about 5 to 10 percent.

The ratio of reactants per mole of alkylphenol can vary from about 1 to 5 moles of aldehyde reactant and 0.5–5 moles of amine reactant. Molar amounts of amine less than one can be used when the amine contains more than one H—N< group, such as in the ethylene polyamines (e.g., tetraethylenepentamine). A more preferred reactant ratio based on one mole of alkylphenol is from 2.5 to 4 moles of aldehyde and from 1.5 to 2.5 moles of amine reactant. A most preferred ratio of reactants is about 2 moles alkylphenol to about 3 moles of aldehyde to about 2 moles of amine reactant. This ratio gives an especially useful product when the alkylphenol is a polybutene-substituted phenol in which the polybutene group has a molecular weight of about 900-1100, the aldehyde is formaldehyde and the amine is N,N-dimethyl-1,3-propanediamine.

The condensation reaction will occur by simply warming the reactant mixture to a temperature sufficient to effect the reaction. The reaction will proceed at temperatures ranging from about 50° to 200° C. A more preferred temperature range is from about 75° to 175° C. When a solvent is employed it is desirable to conduct the reaction at the reflux temperature of the solvent-containing reaction mass. For example, when toluene is used as the solvent, the condensation proceeds at about 100° to 150° C. as the water formed in the reaction co-distills together with the water-immiscible solvent, permitting its removal from the reaction zone. During this water removal portion of the reaction period the water-immiscible solvent is returned to the reaction zone after separating water from it.

The time required to complete the reaction depends upon the reactants employed and the reaction temperature used. Under most conditions the reaction is complete in from about one to 8 hours.

The reaction product is a viscous oil and can be added directly to the crude feed stock prior to distillation, or it can be in the form of a concentrate. Thus, another embodiment of the present invention is an antifouling concentrate containing an additive amount of a condensation product of this invention and a diluent. The amount of condensation product in the concentrate can vary from about 0.1-90 weight percent. A particularly useful mixture is about two-thirds condensation product and one-third diluent. The diluent serves to maintain the concentrate in a liquid form making it easy to handle and to meter into the crude feed stock or distillation column sumps. Preferred diluents are hydrocarbons, especially aromatic hydrocarbons such as benzene, toluene, xylene, and the like, including mixtures thereof. Thus, the amount of condensation product in the concentrate, using a preferred diluent, ranges from 10%-90% and preferably from 35% to 75%.

The condensation products of the present invention have found use in the prior art in lubricating oils as exemplified by U.S. Pat. Nos. 3,368,972 and 3,413,347; and as gasoline detergents as ememplified by U.S. Pat. Nos. 3,649,229 and 3,948,619.

Specifically, U.S. Pat. No. 3,368,972 discloses an improved lubricating oil having high dispersant properties comprising lubricating oil and from 0.05 to 25% by weight of said lubricating oil of a condensation product of (1) a high molecular weight alkyl-substituted hydroxy-aromatic compound wherein the alkyl substituent has a molecular weight of 600-3000, (2) an amine, which contains an HN< group, and (3) an aldehyde wherein the respective molar ratio of reactants is 1:0.1-10:0.1-10. U.S. Pat. No. 3,413,347 discloses the condensation products of an alkylphenol, an aldehyde and a diamine and their use in lubricating oil as ashless lubricating oil dispersants. U.S. Pat. No. 3,649,229 discloses a liquid hydrocarbon combustion fuel containing an amount sufficient to impart improved detergency properties thereto of an additive composition comprising the condensation product of (1) a high molecular weight sulfur free alkyl-substituted hydroxy aromatic compound wherein the alkyl has a molecular weight of from about 600 to about 3000, (2) an amine which contains an amino group having at least one active hydrogen atom and (3) an aldehyde, wherein the respective molar ratio of reactants is 1:0.1-10:0.1-10. U.S. Pat. No. 3,948,619 discloses a liquid hydrocarbon fuel of the gasoline boiling range containing I. The reaction product of:
A. one mole part of an alkylphenol having the formula:

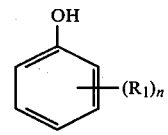

wherein n is an integer from 1 to 2, and $R_1$ is an aliphatic hydrocarbon radical having a molecular weight of from about 400 to 1500;
B. from 1-5 mole parts of an aldehyde having the formula:

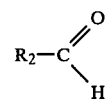

wherein $R_2$ is selected from hydrogen and alkyl radicals containing 1-6 carbon atoms; and
C. from 0.5-5 mole parts of an amine having at least one active hydrogen atom, and
II. normally liquid hydrocarbon polyolefin having an average molecular weight of from about 300 to about 2000.

The addition of the additive to the fuel operates to clean the fuel induction system of an internal combustion engine operating on the additive containing fuel.

The additive agents described above are useful in treating the dialkyl phsophorochloridothioate in amounts sufficient for good reaction with the oxygenated phosphorus compound impurities so that such impurities are maintained at a sufficiently fluid state that they are normally dissolved or suspended in the crude feedstock thereby forming a fairly homogeneous phase. As aforediscussed, under these conditions, the impurities will be prevented or hindered from depositing in and subsequently fouling the process equipment used in the separation and purification of the desired dialkyl phosphorochloridothioate product from the crude feedstock. Further, the impurities can be readily removed from the column bottoms with the waste stream leaving the columns and column reboilers clean. In terms of the total weight of the crude feedstock, the amount of additive can range, in general, from about 0.05 to about 15.0 percent by weight of additive. Although a definite range has been expressed, it should be noted that the lower limit is that only necessary to react with substantially all of the oxygenated phosphorus compound impurities while the upper limit is defined by practical considerations of the separation technique employed, cost of the additive reagent, equipment size, etc. Further, the amount of treating agent required will vary with the amount of impurities present in individual feedstocks. That is, the amount of additive required depends on the degree of purity of the crude. Crudes containing fewer impurities will require treatment with a smaller amount of additive than crudes containing greater amounts of impurities. A more preferred range of additive treatment level is from about 0.01 percent by weight to about 10.0 percent by weight of additive based on the total weight of the crude.

The treatment of crude dialkyl phosphorochloridothioates with Mannich product is generally effective in reasonably short times at somewhat elevated temperatures. However, the time and temperature relationship can be adjusted to produce effective impurity removal at low temperatures and relatively longer contact periods or conversely at high temperatures in relatively shorter contact periods. In general, treatment with condensation product occurs at 100° C. up to temperatures at which the dialkyl phosphorochloridothioate severely thermally degrade. Such higher temperatures should be avoided to prevent danger of explosive decomposition. Generally, temperatures from 100° C. to about 130° C., depending upon the particular alkyl groups in the product dialkyl phosphorochloridothioate, can be used. The product having the shorter alkyl groups should be kept nearer the lower end of the temperature range, while products having longer chain alkyl groups can withstand temperatures nearer the high end of the temperature range. Contact periods from a few minutes to about one hour or more are typical, depending upon the specific additive composition, the separation system, the temperature, etc. It is only necessary to select these parameters and follow the reaction by sampling over time to establish the point at which substantially all of the impurities have disappeared or dissolved in order to establish a treatment procedure.

The prior art contains adequate teaching for separating product dialkyl phosphorochloridothioate from sulfur, reaction mixture, solvent, etc. Such techniques are useful for separating the reaction product of the additive agent and impurities also. Thus, after treatment with a suitable additive the resultant dialkyl phosphorochloridothioate reaction mixture can be heated to distill off the desired dialkyl phosphorochloridothioate. In a preferred aspect of this process after treatment with additive, the resultant mixture of additive and crude dialkyl phosphorochloridothiate containing oxygenated phosphorus impurities is fed to a distillation section of conventional design, and the dialkyl phosphorochloridothioate is taken overhead as a product substantially free of oxygenated phosphorus compound impurities and the reaction product of such impurities with the additive remains with the bottoms product. The distillation section can be designed and operated in a manner such that substantially low losses of product dialkyl phosphorochloridothioate are incurred and fouling of the process equipment due to the presence of oxygenated phosphorus compounds is virtually eliminated.

As a further illustration describing the process of this invention, the following non-limiting examples are provided. The examples are to be considered only illustrative of the process of this invention. All percentages are by weight unless otherwise noted.

COMPARATIVE EXAMPLE 1

This example demonstrates the problem of column reboiler plugging during the separation and purification of product diethyl phosphorochloridothioate from an untreated mixture thereof containing certain phosphorus compound impurities.

Product diethyl phosphorochloridothioate was recovered from untreated crude feedstock by vacuum distillation.

A 4" pyrex pipe packed column having about 8 theoretical separation stages having a feed point at about the mid-point of the column above the reboiler was set up to operate at an overhead condenser pressure of approximately 15 mm Hg absolute and an overhead temperature of approximately 84° C. The pressure below the bottom of the packing was 21 mm Hg and the sump temperature was 132° C., produced by approximately 50–70 psig of steam. A feed rate was typically 6.3 pounds per hour of crude diethyl phosphorochloridothioate from which any reaction solvent and lower boiling impurities had already been removed. The column reboiler was an S.S. American Standard exchanger consisting of 3¾ inch diameter tubes; 2 feet 8 inches in length having a heat transfer surface area of 0.8 square feet. A typical feed to the column taken from the material balance follows:

| Component | Weight % |
|---|---|
| DECTP[a] | 59.23 |
| DECP[b] | 0.19 |
| TETP[c] | 0.13 |
| Sulfur Solubizing Agent[d] | 12.95 |
| Other Phosphorus Compounds | 13.77 |
| Sulfur | 4.4 |
| Antifouling Agent[e] | 0.89 |
| Heavy Impurities Treating Agent | 8.44 |
| | 100.00 |

[a]DECTP is diethyl chlorothiophosphate (i.e., diethyl phosphorochloridothioate)
[b]DECP is diethylchlorophosphate
[c]TETP is triethylthiophosphate
[d]Naphthalenic liquid hydrocarbon
[e]Mannich condensation product Prior to the addition of the condensation product of the present invention, the distillation of crude feed streams, similar to the composition given above but without the antifouling agent were run under the given column conditions. Distillation was continued until plugging of the reboiler unit forced the shutdown of the column. After approximately 37 hours of operation the column reboiler was plugged and operation had to be discontinued. As demonstrated by this test, untreated crude plugged the column reboiler in the distillation column and caused eventual involuntary shutdown of the distillation process.

EXAMPLE 2

As a result of the column plugging problem illustrated in Example 1 above, a column simulation test was designed for the purposes of (1) determining and rating the fouling tendencies of each individual crude feed stock fed into the distillation equipment; and (2) for determining the causes of and means for preventing reboiler fouling. The simulation test showed that the addition of a condensation product of the present invention to a fouling crude, i.e. one that tended to cause severe fouling in the distillation train, greatly reduced its fouling tendencies. The column simulation test (or fouling test) was designed to simulate conditions in the column reboiler of a 1-inch 10 tray glass Oldershaw column. The following procedure was followed:

1. A weighed sample (typically 375 grams) of crude feed stock was deposited into a 500 ml flask and installed on the bottom of the 1-inch 10 tray Oldershaw column.

2. Vacuum was applied to 78 mm Hg absolute pressure while simultaneously heating the flask. Reflux ratio was set at 1:1.

3. Overhead was collected until bottoms temperature reached 110° C., then put on total reflux.

4. Heating was continued to 125° C. and refluxed for 4 hours.

5. Heat was removed and the column allowed to drain.

6. The bottoms were filtered and the flask and filter were observed. The fouling tendencies of the crudes were rated on a scale of 1–5 depending on the weight and acidity of the deposits remaining on the glass reboiler flask walls after 4 hours of operation. A No. 1 rating was the best and indicated no deposits. The fouling scale is set forth below:
1=no fouling, clean filter
2=no fouling, heavy fluid at bottom of flask
3=no fouling, large amounts of filter cake
4=light fouling
5=heavy fouling Experiments showed that the addition of a small amount (typically 0.4 weight percent to about 1.0 weight percent) of the aforedescribed condensation product concentrate comprising approximately two-thirds condensation product and one-third aromatic solvent to a previously rated No. 5 crude feed stock converted the heavy fouling No. 5 rated crude to a non-fouling No. 1 rated crude. In a typical column simulation test, a 375 gram sample of untreated crude feed stock comprising 41.7 weight percent dimethyl phosphorochloridothioate, 3.7 weight percent phosphorus compound impurities, 2.7 weight percent sulfur, 43.1 weight percent solvent and 8.7 weight percent sulfur solubilizing agent was tested in the column simulation test according to the procedure set forth above. The sample crude rated a No. 5 according to the test indicating that it would severely foul the column and/or column reboiler unit when fed into the column. Next, 0.4 weight percent of the aforedescribed concentrate was added to another sample of the same crude and retested in the column simulation test as before. The addition of the treating agent to the previously No. 5 rated crude, produced a No. 1 rating indicating that it would not cause fouling of the distillation equipment. Thus, the column simulation test was successful not only for rating different crude feed stocks according to their propensity to cause fouling in the distillation equipment during separation and purification of product dialkyl phosphorochloridothioate, but also showed that the addition of a suitable condensation product to a crude feed stock previously determined by the column simulation test to cause fouling when fed into the distillation equipment would convert the fouling crude into a non-fouling feed stock.

Having described the invention, one skilled in the art could ascertain various changes and modifications thereof which are within the scope of the disclosed process. Therefore, it is desired to limit the invention only by the lawful scope of the following claims.

I claim:

1. A method for inhibiting or preventing the accumulation of oxygenated phosphorus compound impurities in the distillation columns and column reboiler units associated with the separation and purification of O,O-dialkyl phosphorochloridothioates from a crude feed stock containing said O,O-dialkyl phosphorochloridothioates admixed with deposit-forming and fouling-causing oxygenated phosphorus compound impurities which comprises distilling said O,O-dialkyl phosphorochloridothioate containing feed stock in the presence of a minor proportion of the reaction product of:

A. one mole part of an alkylphenol having the formula:

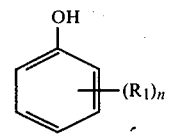

wherein n is an integer from 1 to 2, and $R_1$ is an aliphatic hydrocarbon radical having a molecular weight of from about 400 to 1500;

B. from 1–5 mole parts of an aldehyde having the formula:

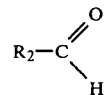

wherein $R_2$ is selected from hydrogen and alkyl radicals containing 1–6 carbon atoms; and C. from 0.5–5 mole parts of an amine having at least one H—N< group.

2. The method of claim 1 wherein said O,O-dialkyl phosphorochloridothioate is O,O-di($C_1$–$C_8$ alkyl) phosphorochloridothioate.

3. The method of claim 1 wherein said O,O-dialkyl phosphorochloridothioate is diethyl phosphorochloridothioate.

4. The method of claim 1 wherein said O,O-dialkyl phosphorochloridothioate is dimethyl phosphorochloridothioate.

5. The method of claim 1 wherein said oxygenated phosphorus compound impurity is a diethyl or dimethyl phosphate impurity.

6. The method of claim 1 wherein said oxygenated phosphorus compound impurity is diethyl phosphate impurity.

7. The method of claim 1 wherein said oxygenated phosphorus compound impurity is diethyl chlorophosphate.

8. The method of claim 1 in which said distillation is carried out in the presence of at least about 0.05 weight percent of said reaction product based on the total weight of said feedstock.

9. The method of claim 1 in which said distillation carried out in the presence of at least from about 0.05 weight percent to about 15.0 weight percent of said reaction product based on the total weight of said feedstock.

10. The method of claim 1 wherein said aldehyde is selected from formaldehyde and paraformaldehyde.

11. The method of claim 10 wherein $R_1$ is a polyalkene group having a molecular weight of from 400 to 1500.

12. The method of claim 11 wherein $R_1$ is a polybutene group having a molecular weight of from 900 to 1100.

13. The method of claim 11 wherein $R_1$ is a polypropylene group having a molecular weight of from 900 to 1100.

14. The method of claim 11 wherein said amine is an alkylene polyamine of the formula:

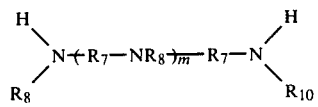

wherein $R_8$, $R_9$ and $R_{10}$ are selected from hydrogen and lower alkyl radicals containing 1–4 carbon atoms, and $R_7$ is a divalent saturated aliphatic hydrocarbon radical containing from 2 to about 4 carbon atoms and m is an integer from 0 to about 4.

15. The method of claim 14 wherein said alkylene polyamine is an ethylene polyamine selected from ethylene diamine, diethylene triamine, triethylene tetramine, tetraethylene pentamine, and mixtures thereof.

16. The method of claim 15 wherein said alkylphenol is a polybutene-substituted phenol.

17. The method of claim 15 wherein said alkylphenol is a polypropylene-substituted phenol.

18. The method of claim 10 wherein said amine is a diamine having the formula:

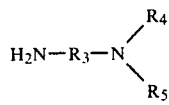

wherein $R_3$ is a divalent alkylene radical containing 1–6 carbon atoms, and $R_4$ and $R_5$ are selected from the group consisting of alkyl radicals containing from 1–6 carbon atoms and radicals having the formula:

$$-R_6-X$$

wherein $R_6$ is a divalent alkylene radical containing from 1–6 carbon atoms, and X is selected from the group consisting of the hydroxyl radical and the amine radical.

19. The method of claim 18 wherein said diamine is N,N-dimethyl-1,3-propandiamine.

20. The method of claim 19 wherein said alkylphenol is a polybutene-substituted phenol wherein said polybutene substituent has an average molecular weight of from about 900–1100.

21. The method of claim 20 wherein said reaction product is formed by the reaction of about 2 mole parts of said polybutene-substituted phenol, about 3 mole parts of said formaldehyde and about 2 mole parts of said N,N-dimethyl-1,3-propanediamine.

* * * * *

UNITED STATES PATENT AND TRADEMARK OFFICE
CERTIFICATE OF CORRECTION

PATENT NO. : 4,311,562
DATED : January 19, 1982
INVENTOR(S) : Ellis B. Rifkin

It is certified that error appears in the above-identified patent and that said Letters Patent are hereby corrected as shown below:

Column 3, line 38 - "4" should be -- 3 --
Column 5, line 39 - "H-N group" should be -- H-N< group --
Column 5, line 57 -

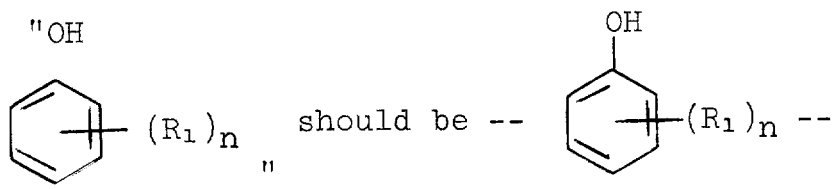

Column 6, line 10 - "H-N group" should be -- H-N< group --
Column 10, line 2 - "$_{45}$" should -- $R_5$ --
Column 16, Claim 9, line 1 - after "distillation" insert -- is--
Column 18, Claim 19, line 2 - "propandiamine" should be
 -- propanediamine --

Signed and Sealed this

Sixth Day of April 1982

|SEAL|

Attest:

GERALD J. MOSSINGHOFF

Attesting Officer    Commissioner of Patents and Trademarks